United States Patent
Ben Nun

(10) Patent No.: US 8,956,409 B2
(45) Date of Patent: *Feb. 17, 2015

(54) ACCOMMODATING INTRAOCULAR LENS ASSEMBLIES AND ACCOMMODATION MEASUREMENT IMPLANT

(75) Inventor: Joshua Ben Nun, D.N. Vitkin (IL)

(73) Assignee: Nulens Ltd., Herzliya Pituah (IL)

( * ) Notice: Subject to any disclaimer, the term of this patent is extended or adjusted under 35 U.S.C. 154(b) by 685 days.

This patent is subject to a terminal disclaimer.

(21) Appl. No.: 12/906,598

(22) Filed: Oct. 18, 2010

(65) Prior Publication Data
US 2011/0035002 A1 Feb. 10, 2011

Related U.S. Application Data

(63) Continuation of application No. 11/568,416, filed as application No. PCT/IL2005/000456 on May 1, 2005, now Pat. No. 7,842,087.

(60) Provisional application No. 60/589,567, filed on Jul. 21, 2004.

(30) Foreign Application Priority Data

Apr. 29, 2004 (IL) .......................................... 161706

(51) Int. Cl.
  *A61F 2/16* (2006.01)
(52) U.S. Cl.
  CPC ............. *A61F 2/1616* (2013.01); *A61F 2/1648* (2013.01); *A61F 2/1613* (2013.01); *A61F 2/1635* (2013.01)
  USPC ....................................................... 623/6.37
(58) Field of Classification Search
  USPC ............................................... 623/6.37–6.41
  See application file for complete search history.

(56) References Cited

U.S. PATENT DOCUMENTS

| 3,950,082 A | 4/1976 | Volk |
| 4,122,556 A | 10/1978 | Poler |

(Continued)

FOREIGN PATENT DOCUMENTS

| EP | 0 156 472 A | 10/1985 |
| EP | 0637503 B1 | 10/1998 |

(Continued)

OTHER PUBLICATIONS

Chu, Ralph Y. and Buliano, Megan, Accommodating IOLS by Ralph Chu et al, Cataract & Refractive Surgery Today, May 2004.

(Continued)

*Primary Examiner* — Corrine M McDermott
*Assistant Examiner* — Joshua Levine
(74) *Attorney, Agent, or Firm* — Morgan, Lewis & Bockius LLP

(57) ABSTRACT

A haptics system for retaining an accommodating intraocular lens (AIOL) in a human eye has an anterior surface and a posterior surface, and at least one shape memory optical element resiliently elastically deformable between a natural shape with a first Diopter strength and a deformed shape with a second Diopter strength different than the first Diopter strength whereby the AIOL has a continuously variable Diopter strength between a minimum Diopter strength for distance vision purposes and a maximum Diopter strength for near vision purposes. The haptics system includes a main body with a longitudinal axis intended to be co-directional with the human eye's visual axis and at least two haptics tangentially extending from said main body in opposite directions in a plane perpendicular to the haptics system's longitudinal axis, and each with at least one pointed puncturing member for penetrating the tough connective tissue of the human eye's sclera for self-anchoring implantation in the human eye's annular ciliary sulcus at at least two spaced apart stationary anchor points for retaining the AIOL along the human eye's visual axis.

6 Claims, 7 Drawing Sheets

(56) References Cited

U.S. PATENT DOCUMENTS

| | | |
|---|---|---|
| 4,254,509 A | 3/1981 | Tennant |
| 4,298,994 A | 11/1981 | Clayman |
| 4,340,979 A | 7/1982 | Kelman |
| 4,409,690 A | 10/1983 | Gess |
| 4,409,691 A | 10/1983 | Levy |
| 4,445,998 A | 5/1984 | Kanda et al. |
| 4,446,581 A | 5/1984 | Blake |
| 4,494,254 A | 1/1985 | Lopez |
| 4,530,117 A | 7/1985 | Kelman |
| RE31,963 E | 8/1985 | Kelman |
| 4,556,998 A | 12/1985 | Siepser |
| 4,575,374 A | 3/1986 | Anis |
| 4,581,033 A | 4/1986 | Callahan |
| 4,589,147 A | 5/1986 | Nevyas |
| 4,591,358 A | 5/1986 | Kelman |
| 4,615,701 A | 10/1986 | Woods |
| 4,671,283 A | 6/1987 | Hoskin et al. |
| 4,676,794 A | 6/1987 | Kelman |
| 4,750,904 A | 6/1988 | Price, Jr. |
| 4,808,181 A | 2/1989 | Kelman |
| 4,842,601 A | 6/1989 | Smith |
| RE33,039 E | 8/1989 | Arnott |
| 4,865,601 A | 9/1989 | Caldwell et al. |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,957,505 A | 9/1990 | McDonald |
| 4,969,897 A | 11/1990 | Kalb |
| 4,976,732 A | 12/1990 | Vorosmarthy |
| 4,990,159 A | 2/1991 | Kraff |
| 5,026,373 A | 6/1991 | Ray |
| 5,078,742 A | 1/1992 | Dahan |
| 5,171,268 A | 12/1992 | Ting et al. |
| 5,176,701 A | 1/1993 | Dusek et al. |
| 5,275,623 A | 1/1994 | Sarfarazi |
| 5,282,851 A | 2/1994 | Jacob-LaBarre |
| 5,288,293 A | 2/1994 | O'Donnell, Jr. |
| 5,336,262 A | 8/1994 | Chu |
| 5,346,502 A | 9/1994 | Estabrook et al. |
| 5,476,512 A | 12/1995 | Sarfarazi |
| 5,476,514 A | 12/1995 | Cumming |
| 5,476,515 A | 12/1995 | Kelman et al. |
| 5,480,426 A | 1/1996 | Chu |
| 5,484,447 A | 1/1996 | Waldock et al. |
| 5,489,302 A | 2/1996 | Skottun |
| 5,496,366 A | 3/1996 | Cumming |
| 5,522,891 A | 6/1996 | Klaas |
| 5,567,365 A | 10/1996 | Weinschenk et al. |
| 5,571,177 A | 11/1996 | Deacon et al. |
| 5,584,304 A | 12/1996 | Brady |
| 5,607,472 A | 3/1997 | Thompson |
| 5,628,795 A | 5/1997 | Langerman |
| 5,674,282 A | 10/1997 | Cumming |
| 5,684,637 A | 11/1997 | Floyd |
| 5,722,952 A | 3/1998 | Schachar |
| 5,752,960 A | 5/1998 | Nallakrishnan |
| 5,766,244 A | 6/1998 | Binder |
| 5,843,188 A | 12/1998 | McDonald |
| 5,871,455 A | 2/1999 | Ueno |
| 5,895,610 A | 4/1999 | Chang |
| 5,919,230 A | 7/1999 | Sambursky |
| 5,968,094 A | 10/1999 | Werblin et al. |
| 5,984,962 A | 11/1999 | Anello |
| 6,007,579 A | 12/1999 | Lipshitz et al. |
| 6,027,531 A | 2/2000 | Tassignon |
| 6,051,024 A | 4/2000 | Cumming |
| 6,110,202 A | 8/2000 | Barraquer et al. |
| 6,117,171 A | 9/2000 | Skottun |
| 6,129,759 A | 10/2000 | Chambers |
| 6,164,282 A | 12/2000 | Gwon et al. |
| 6,193,750 B1 | 2/2001 | Cumming |
| 6,197,057 B1 | 3/2001 | Peyman et al. |
| 6,197,059 B1 | 3/2001 | Cumming |
| 6,200,342 B1 | 3/2001 | Tassignon |
| 6,280,469 B1 | 8/2001 | Terry et al. |
| 6,280,471 B1 | 8/2001 | Peyman et al. |
| 6,299,618 B1 | 10/2001 | Sugiura |
| 6,299,641 B1 | 10/2001 | Woods |
| 6,342,073 B1 | 1/2002 | Cumming et al. |
| 6,387,126 B1 | 5/2002 | Cumming |
| 6,406,494 B1 | 6/2002 | Laguette et al. |
| 6,423,094 B1 | 7/2002 | Sarfarazi |
| 6,443,984 B1 | 9/2002 | Jahn et al. |
| 6,443,985 B1 | 9/2002 | Woods |
| 6,464,725 B2 | 10/2002 | Skotton |
| 6,488,708 B2 | 12/2002 | Sarfarazi |
| 6,494,910 B1 | 12/2002 | Ganem et al. |
| 6,494,911 B2 | 12/2002 | Cumming |
| 6,503,276 B2 | 1/2003 | Lang et al. |
| 6,506,212 B2 | 1/2003 | Zhou et al. |
| 6,520,691 B2 | 2/2003 | Nomura et al. |
| 6,524,340 B2 | 2/2003 | Israel |
| 6,554,860 B2 | 4/2003 | Hoffmann et al. |
| 6,570,718 B2 | 5/2003 | Nomura et al. |
| 6,596,026 B1 | 7/2003 | Gross et al. |
| 6,599,317 B1 | 7/2003 | Weinschenk, III et al. |
| 6,605,093 B1 | 8/2003 | Blake |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,739,722 B2 | 5/2004 | Laguette et al. |
| 6,749,634 B2 | 6/2004 | Hanna |
| 6,790,232 B1 | 9/2004 | Lang |
| 6,849,091 B1 | 2/2005 | Cumming |
| 6,960,231 B2 | 11/2005 | Tran |
| 6,972,033 B2 | 12/2005 | McNicholas |
| 7,008,449 B2 | 3/2006 | Willis et al. |
| 7,025,783 B2 | 4/2006 | Brady et al. |
| 7,037,338 B2 | 5/2006 | Nagamoto |
| 7,097,660 B2 | 8/2006 | Portney |
| 7,118,597 B2 | 10/2006 | Miller et al. |
| 7,122,053 B2 | 10/2006 | Esch |
| 7,137,994 B2 | 11/2006 | De Juan, Jr. |
| 7,220,279 B2 | 5/2007 | Nun |
| 7,261,737 B2 | 8/2007 | Esch et al. |
| 7,278,739 B2 | 10/2007 | Shadduck |
| 7,350,916 B2 | 4/2008 | Hong et al. |
| 7,815,678 B2 | 10/2010 | Ben Nun |
| 7,842,087 B2 | 11/2010 | Ben Nun |
| 7,854,764 B2 | 12/2010 | Ben Nun |
| 7,976,520 B2 | 7/2011 | Ben Nun |
| 7,998,199 B2 | 8/2011 | Ben Nun |
| 8,048,156 B2 | 11/2011 | Geraghty et al. |
| 2002/0103535 A1 | 8/2002 | Portney |
| 2002/0103537 A1 | 8/2002 | Willis et al. |
| 2003/0060881 A1 | 3/2003 | Glick et al. |
| 2003/0097177 A1 | 5/2003 | Tran |
| 2003/0109926 A1 | 6/2003 | Portney |
| 2003/0149480 A1 | 8/2003 | Shadduck |
| 2004/0073304 A1 | 4/2004 | Weinschenk, III et al. |
| 2004/0148022 A1 | 7/2004 | Eggleston |
| 2004/0169816 A1 | 9/2004 | Esch |
| 2004/0181279 A1 | 9/2004 | Ben Nun |
| 2005/0090896 A1 | 4/2005 | Ben Nun |
| 2005/0177229 A1 | 8/2005 | Boxer Wachler |
| 2006/0069431 A1 | 3/2006 | Graney et al. |
| 2006/0069433 A1 | 3/2006 | Nun |
| 2006/0074487 A1 | 4/2006 | Gilg |
| 2007/0027538 A1 | 2/2007 | Aharoni et al. |
| 2007/0027541 A1 | 2/2007 | Aharoni et al. |
| 2007/0088433 A1 | 4/2007 | Esch et al. |
| 2007/0093891 A1 | 4/2007 | Tabernero |
| 2007/0123981 A1 | 5/2007 | Tassignon |
| 2007/0129799 A1 | 6/2007 | Schedler |
| 2007/0129801 A1 | 6/2007 | Cumming |
| 2007/0129803 A1 | 6/2007 | Cumming |
| 2007/0185574 A1 | 8/2007 | Ben Nun |
| 2007/0244561 A1 | 10/2007 | Ben Nun |
| 2008/0004699 A1 | 1/2008 | Ben Nun |
| 2008/0188930 A1 | 8/2008 | Mentak et al. |
| 2008/0300680 A1 | 12/2008 | Ben Nun |

(56) References Cited

U.S. PATENT DOCUMENTS

| | | |
|---|---|---|
| 2009/0198247 A1 | 8/2009 | Ben Nun |
| 2009/0264998 A1 | 10/2009 | Mentak et al. |
| 2010/0121444 A1 | 5/2010 | Ben Nun |

FOREIGN PATENT DOCUMENTS

| | | |
|---|---|---|
| EP | 1 321 112 A | 6/2003 |
| FR | 2 794 965 | 12/2000 |
| JP | 2005007029 | 1/2005 |
| TW | 523408 | 3/2003 |
| WO | WO 83/00998 | 3/1983 |
| WO | WO 94/28825 | 12/1994 |
| WO | WO 95/20367 | 8/1995 |
| WO | WO 98/05273 | 2/1998 |
| WO | WO 98/10717 | 3/1998 |
| WO | WO 99/62434 | 12/1999 |
| WO | WO 00/30566 | 6/2000 |
| WO | WO 00/61036 | 10/2000 |
| WO | WO 00/66037 | 11/2000 |
| WO | WO 01/08606 | 2/2001 |
| WO | WO 01/60286 | 8/2001 |
| WO | WO 02/065951 | 8/2002 |
| WO | WO 03/000154 | 1/2003 |
| WO | WO 03/015669 | 2/2003 |
| WO | WO 2005/104994 | 11/2005 |
| WO | WO 2006/040759 | 4/2006 |
| WO | WO 2006/103674 | 10/2006 |
| WO | WO 2007/048615 | 5/2007 |
| WO | WO 2008/023379 | 2/2008 |
| WO | WO 2008/083283 A2 | 7/2008 |
| WO | WO 2008/097915 | 8/2008 |
| WO | WO 2008/107882 | 9/2008 |
| WO | WO 2009/122409 | 10/2009 |
| WO | WO 2010/010565 | 1/2010 |
| WO | WO 2012/023133 | 2/2012 |

OTHER PUBLICATIONS

Notification of Transmittal of the International Preliminary Report on Patentability for PCT/IL2009/000728 filed Jul. 26, 2009 (having a priority date of Jul. 24, 2008).

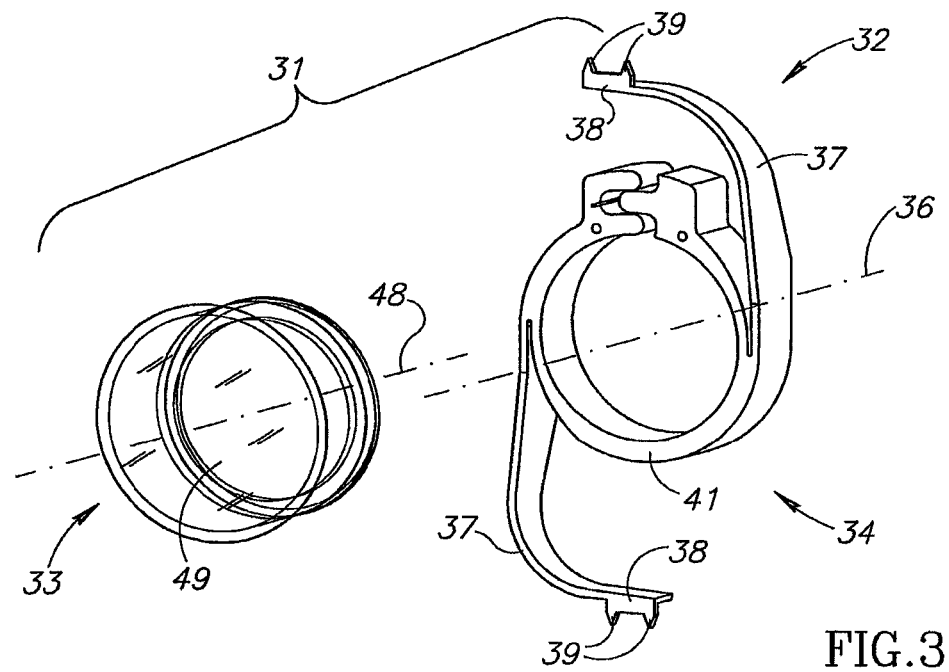
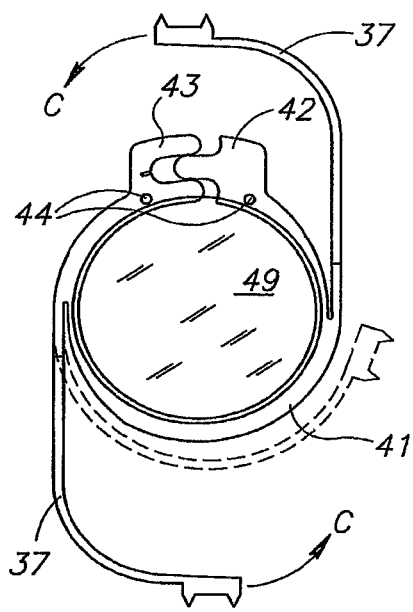
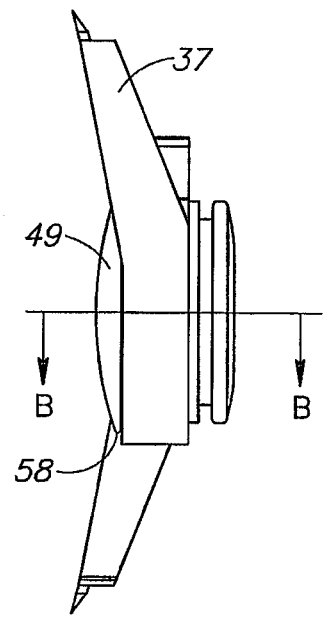
FIG.3
FIG.4
FIG.5

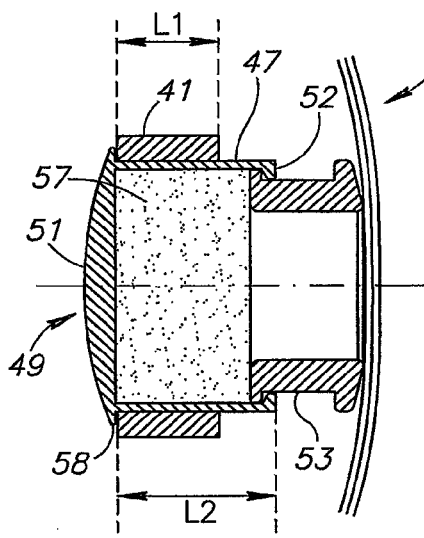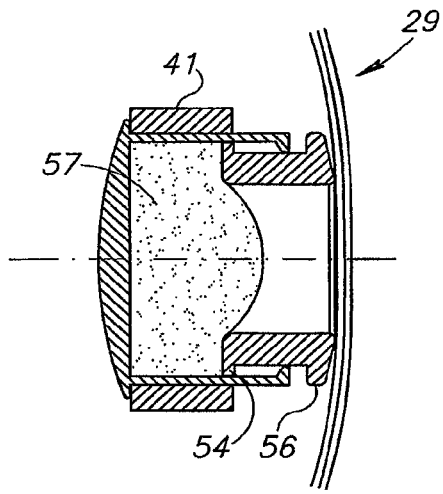
FIG.6　　　　　　　FIG.7
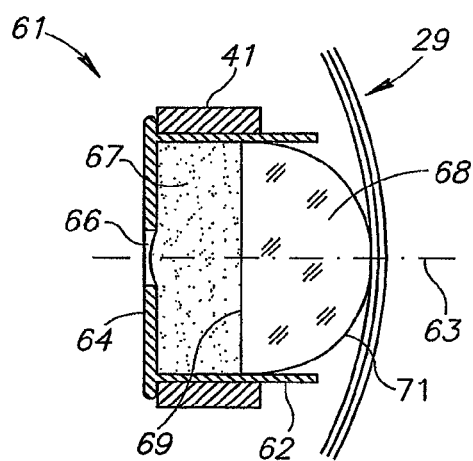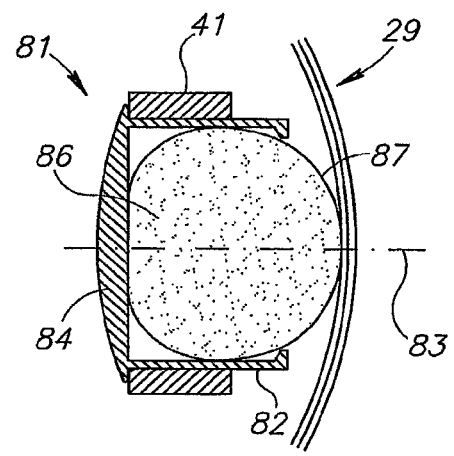
FIG.8　　　　　　　FIG.9

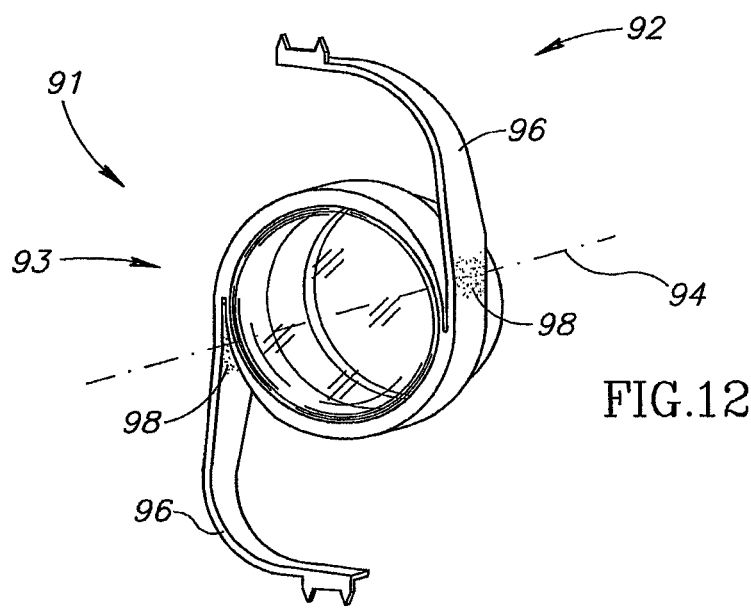
FIG.12
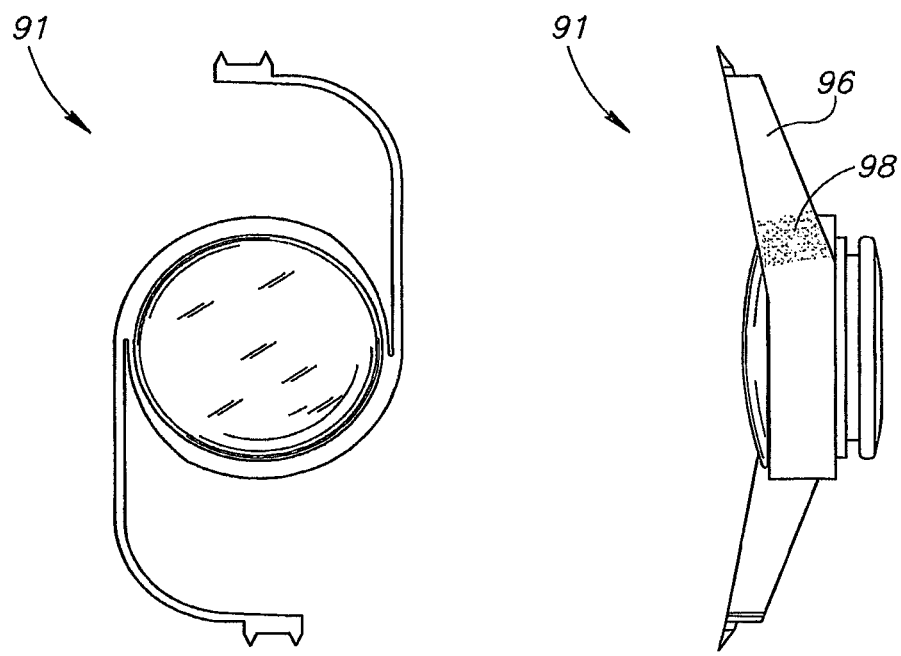
FIG.13                    FIG.14

ACCOMMODATING INTRAOCULAR LENS ASSEMBLIES AND ACCOMMODATION MEASUREMENT IMPLANT

CROSS-REFERENCE TO RELATED APPLICATIONS

This application is a Continuation Application of U.S. patent application Ser. No. 11/568,416, filed Oct. 27, 2006, which issued as U.S. Pat. No. 7,842,087 on Nov. 30, 2010, and which was a national stage application for PCT/IL2005/000456 filed May 1, 2005, claiming priority to IL161706 filed Apr. 29, 2004 and to U.S. 60/589,567 filed Jul. 21, 2004, all of which are incorporated herein by reference in their entirety.

TECHNICAL FIELD

The invention pertains to accommodating intraocular lens assemblies and apparatus for measuring accommodation in an experimental set-up including an animal eye.

BACKGROUND OF THE INVENTION

Commonly owned PCT International Application No. PCT/IL02/00693 entitled Accommodating Lens Assembly and published under PCT International Publication No. WO 03/015669 illustrates and describes accommodating intraocular lens (hereinafter AIOL) assemblies, the contents of which are incorporated herein by reference. The AIOL assemblies include a haptics system adapted to be securely fixed in a human eye's annular ciliary sulcus at at least two spaced apart stationary anchor points so that it may act as a reference plane for an AIOL of continuously variable Diopter strength affected by a human eye's capsular diaphragm acting thereagainst from a posterior direction and under control of its sphincter-like ciliary body. The haptics system includes a rigid planar haptics plate with a telescoping haptics member for sliding extension. The haptics plate and the haptics member are preferably self-anchoring as illustrated and described in commonly owned PCT International Application No. PCT/IL02/00128 entitled Intraocular Lens and published under PCT International Publication No. WO 02/065951, the contents of which are incorporated herein by reference. However, the haptics systems are not readily foldable thereby requiring a relatively large incision for insertion of an AIOL assembly into a human eye. Still further, anterior movements of a human eye's capsular diaphragm may lead to bulging of an AIOL assembly in an anterior direction instead of affecting an AIOL's Diopter strength. Moreover, the AIOL assemblies do not afford in situ re-adjustment along a human eye's visual axis which may be required due to capsular contraction thereby requiring that a subject resort to wearing spectacles or undergoing a surgical procedure for correcting his eyesight.

U.S. Pat. No. 6,739,722 to Laguette et al. illustrates and describes apparatus for measuring accommodation of a human eye including a target, a Badal lens, and a viewing aperture where the Badal lens and the viewing aperture are positioned so that when the target moves towards or away from the lens, the apparent size of the target remains constant to a subject looking in the viewing aperture regardless of the distance the target moves.

BRIEF SUMMARY OF THE INVENTION

Generally speaking, the present invention pertains to AIOL assemblies for self-anchoring implantation in a human eye's annular ciliary sulcus at at least two and preferably more spaced apart stationary anchor points and having an AIOL of variable Diopter strength capable of in situ selective displacement along the human eye's visual axis for enabling accurate eyesight correction in general, and for compensating for capsular contraction in particular. The AIOLs include at least one shape memory optical element resiliently elastically deformable between a natural shape with a first Diopter strength and a deformed shape with a second Diopter strength different than the first Diopter strength whereby the AIOL has a continuously variable Diopter strength between a minimum Diopter strength for distance vision purposes and a maximum Diopter strength for near vision purposes. The first Diopter strength can be greater than the second Diopter strength or vice versa.

The AIOL assemblies can be implemented in either a two component construction including a discrete haptics system for selectively retaining a discrete AIOL or a unitary construction including a haptics system integrally formed with an AIOL. Axial re-positioning of a two component AIOL assembly involves displacement of its AIOL relative to its haptics system which remains stationary relative to its stationary anchor points. Against that, axial re-positioning of a unitary AIOL assembly involves adjusting the position of the portion of its haptics system holding its AIOL relative to its stationary anchor points. In the latter case, this is achieved by the haptics system including haptics plastically deformable on heating to a so-called glass transmission temperature higher than a human eye's normal 36° C. temperature but sufficiently low not to damage a human eye's internal structures by irradiation with selective electromagnetic radiation.

The present invention also pertains to an accommodation measurement implant (AMI) for determining accommodation and the accommodation forces in an experimental set-up including an animal eye.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 3 is an exploded perspective view of a two component AIOL assembly including a discrete haptics system and a discrete natural low Diopter strength AIOL in accordance with the present invention;

FIG. 4 is an assembled front view of FIG. 3's AIOL assembly;

FIG. 5 is an assembled side view of FIG. 3's AIOL assembly;

FIG. 6 is a longitudinal cross section view of FIG. 3's AIOL in its natural extended position along line B-B in FIG. 5;

FIG. 7 is a longitudinal cross section view of FIG. 3's AIOL in a compressed position along line B-B in FIG. 5;

FIG. 8 is a longitudinal cross sectional view of another discrete natural low Diopter strength AIOL in its natural state in accordance with the present invention;

FIG. 9 is a longitudinal cross sectional view of a natural discrete high Diopter strength AIOL in its natural state in accordance with the present invention;

FIG. 12 is a perspective view of a unitary AIOL assembly in accordance with the present invention;

FIG. 13 is a front view of FIG. 12's AIOL assembly;

FIG. 14 is a side view of FIG. 12's AIOL assembly;

DETAILED DESCRIPTION OF THE INVENTION

Figure 1:
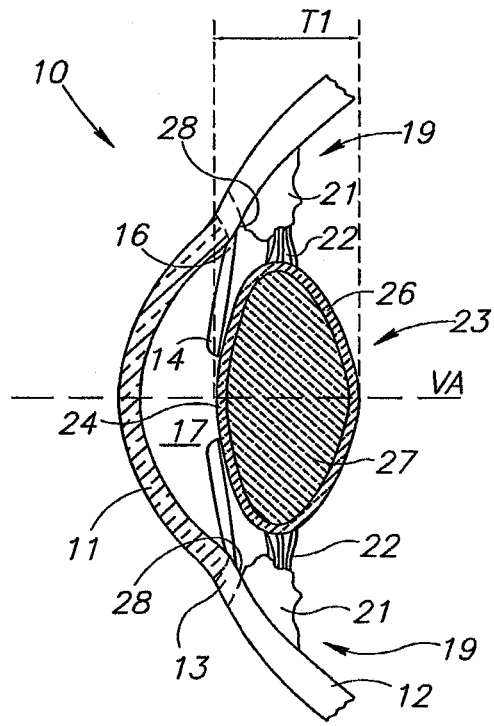
FIG. 1 is a cross section view of an anterior part of a human eye in its natural near vision condition in an axial plane of the human body.
Figure 2:
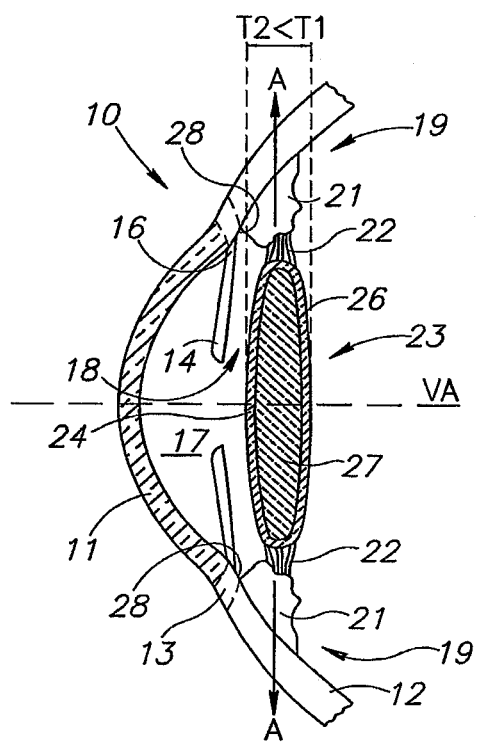
FIG. 2 is a cross section view of an anterior part of a human eye in its natural distance vision condition in an axial plane of the human body.

FIGS. 1 and 2 are cross section views of an anterior part of a human eye 10 having a visual axis VA in its natural near and distance vision conditions, respectively, in an axial plane of the human body. The human eye 10 has a cornea 11 peripherally connected to a spherical exterior body made of tough connective tissue known as the sclera 12 at an annular sclerocorneal juncture 13. An iris 14 inwardly extends into the human eye 10 from its root 16 at the sclero-corneal juncture 13 to divide the human eye's anterior part into an anterior chamber 17 and a posterior chamber 18. A sphincter-like peripheral structure known as the ciliary body 19 includes ciliary processes housing ciliary muscles 21 fired by parasympathetic nerves. The ciliary muscles 21 are connected to zonular fibers 22 which in turn are peripherally connected to the equatorial edge of a membrane known as the capsular bag 23 with an anterior capsule 24 and a posterior capsule 26 enrobing a natural crystalline lens 27. The iris's root 16 and the ciliary body 19 delimit a portion of the interior surface of the sclera 12 at the sclero-corneal juncture 13 known as the ciliary sulcus 28. Remnants of the anterior capsule 24 which may remain after extraction of the natural crystalline lens 27 and the intact posterior capsule 26 are referred to hereinafter as the capsular diaphragm 29. Contraction of the ciliary body 19 allows the lens 27 to thicken to its natural thickness T1 along the visual axis VA for greater positive optical power for near vision (see FIG. 1). Relaxation of the ciliary body 19 tensions the zonular fibers 22 which draws the capsular bag 23 radially outward as shown by arrows A for compressing the lens 27 to shorten its thickness along the visual axis VA to T2<T1 for lower positive optical power for distance vision (see FIG. 2).

FIGS. 3-5 show a two part AIOL assembly 31 made from suitable bio-compatible material such as PMMA, and including a haptics system 32 for self-anchoring implantation in a human eye's ciliary sulcus 28 for retaining an AIOL 33 therein for enabling spectacle free vision over the nominal range of human vision. The haptics system 32 includes a tubular main body 34 with an axial length L1 along a longitudinal axis 36 (see FIG. 6), and a pair of diametrically opposite haptics 37 tangentially extending therefrom in opposite directions in a front view of the haptics system 32. The haptics 37 have a pair of parallel and opposite attachment plates 38 with pointed penetrating members 39 of sufficient strength for forced penetration into the tough connective tissue of a human eye's sclera 12. The penetrating members 39 are preferably dimensioned so as to penetrate slightly more than half of a sclera's thickness of about 1 mm.

The main body 34 is in the form of a flexible split ring 41 with a male end 42 for releasable interference fit into a complementary female end 43 such that the main body 34 is capable of assuming a clamping state for tightly clamping the AIOL 33 therein. The male end 42 and the female end 43 are each provided with an axially directed bore 44 such that the split ring 41 can be prized apart by a suitable ophthalmic surgical tool (not shown) to an unclamping state for enabling axial displacement of the AIOL 33 for positioning purposes for compensating for capsular contraction, its entire replacement if necessary, and the like.

The haptics 37 have a thin profile in a plane perpendicular to the longitudinal axis 36 such that they are sufficiently flexible for encircling around the main body 34 in a direction shown by arrow C for facilitating insertion of the haptics system 32 through a relatively small incision into a human eye. FIG. 4 includes a haptics 37 in dotted lines for showing its encircling around the main body 34. The haptics 37 have a wide profile along the longitudinal axis 36 such that they are rigid against a compressive force therealong. The wide profile preferably tapers from a haptics' proximal end 37A adjacent the main body 34 towards its distal end 37B remote therefrom.

The AIOL 33 includes a tubular casing 47 with an axial length L2 along a longitudinal axis 48, a leading optically clear aperture lens 49 with an anterior surface 51, and a trailing flange 52. The casing's axial length L2 is longer than the main body's axial length L1 such that the main body 34 is capable of fully contacting the casing 47 along an adjustment stroke longer than the main body's axial length L1. The casing 47 slidingly supports a tubular piston-like member 53 with a leading flange 54 and a trailing flange 56 acting as a posterior surface against which a human eye's capsular diaphragm 29 bears. The AIOL 33 houses a shape memory optical element 57 made from soft gel or a fluid or gas filled membrane. The soft gel or fluid may be silicone based or water based, for example, Balanced Salt Solution (BSS), or any other biocompatible transparent liquid having a refractive index similar to that of the natural crystalline lens 27 or greater. The AIOL 33 includes a flange 58 for abutting against the main body 34 to stop displacement of the AIOL 33 in a posterior direction.

The optical element 57 has a natural disc shape with a natural low Diopter strength for distance vision purposes and which urges the piston-like member 53 to a natural extended position (see FIG. 6). The optical element 57 is capable of being resiliently elastically deformed to a deformed shape by a force imparted by a human eye's capsular diaphragm on relaxation of its ciliary body acting against the piston-like member 53 in an anterior direction such that the piston-like member 53 assumes a compressed position with some of the optical element 57 bulging thereinto for rendering a high Diopter strength for near vision purposes (see FIG. 7). The piston-like member 53 is urged from its compressed position outwards to its natural extended position by the optical element 57 reverting to its natural shape on constriction of a human eye's ciliary body. Thus, the AIOL has a continuous variable Diopter strength between a minimum Diopter strength suitable for distance vision purposes and a maximum Diopter strength suitable for near vision purposes depending on the degree of compression of the piston-like member 53 in the casing 47.

FIG. 8 shows an AIOL 61 also suitable for deployment in the haptics system 32 for correcting human eyesight. The AIOL 61 includes a tubular casing 62 with a longitudinal axis 63, and a flat aperture lens 64 constituting an anterior surface and having a central aperture 66. The casing 62 houses a shape memory optical element 67 of a natural disc shape, and a semi-spherical transparent piston-like member 68 having a flat surface 69 juxtaposed against the optical element 67 and a convex shaped posterior surface 71 against which a human eye's capsular diaphragm 29 directly bears for affecting the AIOL's Diopter strength. The optical element 67 has a natural low Diopter strength and is capable of being resiliently elastically deformed to a deformed shape with some of it bulging through the central aperture 66 on relaxation of a human eye's ciliary body for increasing the AIOL's Diopter strength.

FIG. 9 shows an AIOL 81 also suitable for deployment in the haptics system 32 for correcting eyesight. The AIOL 81 includes a tubular casing 82 with a longitudinal axis 83, and a plano-convex aperture lens 84 constituting an anterior surface. The casing 82 houses a shape memory optical element 86 with a natural spherical shape and a posterior surface 87 against which a human eye's capsular diaphragm 29 directly bears for affecting the AIOL's Diopter strength. The optical element 86 has a natural high Diopter strength and is capable of being resiliently elastically deformed to a compressed shape on relaxation of a human eye's ciliary body urging its capsular diaphragm 29 against the posterior surface 87 in an anterior direction for decreasing the AIOL's Diopter strength in a similar fashion as the natural crystalline lens 27.

Figure 10:
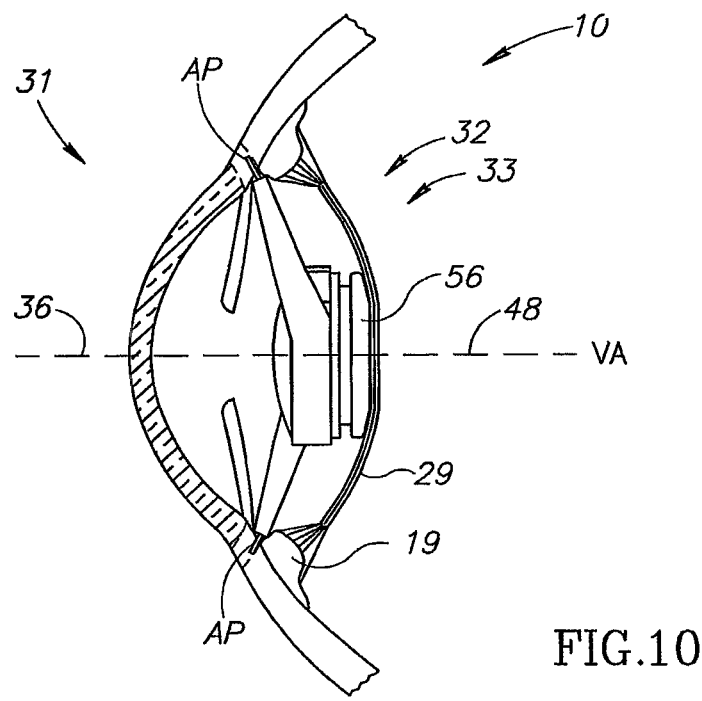
FIG. 10 is a cross section view of an anterior part of a human eye showing an initial position of FIG. 3's AIOL assembly along the human eye's visual axis in an axial plane of the human body.
Figure 11:
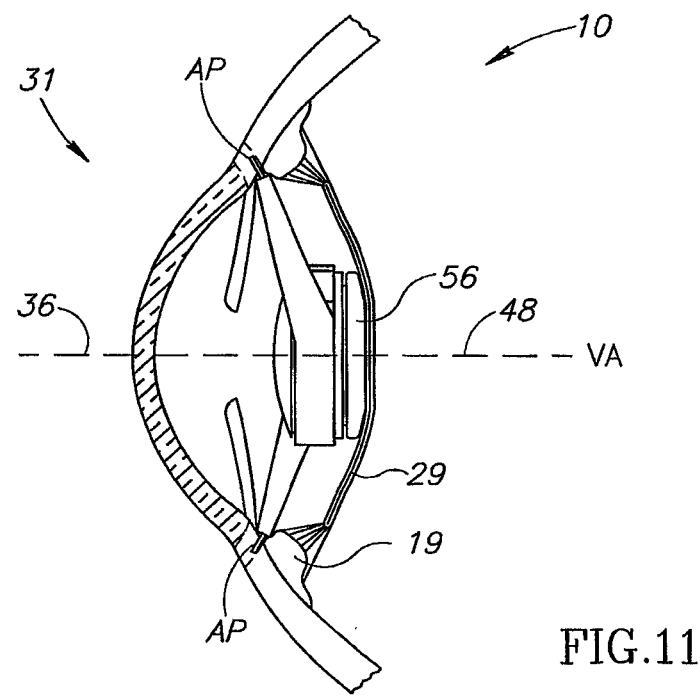
FIG. 11 is a cross section view of an anterior part of a human eye showing a subsequent position of FIG. 3's AIOL assembly along the human eye's visual axis for compensating for capsular contraction in an axial plane of the human body.
Figure 15:
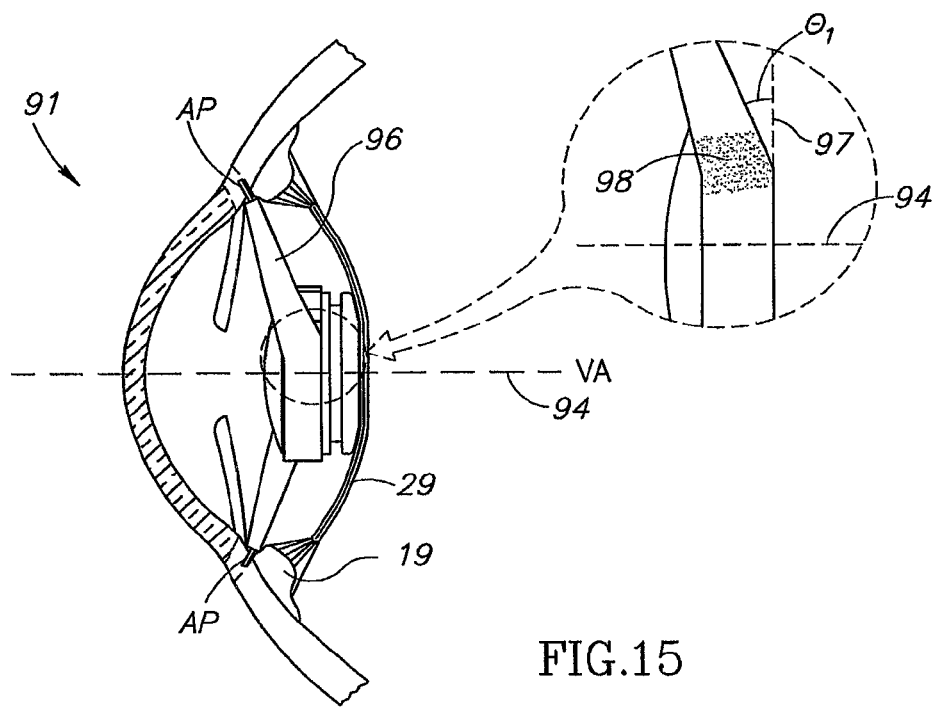
FIG. 15 is a cross section view of an anterior part of a human eye showing an initial position of FIG. 12's AIOL assembly along the human eye's visual axis in an axial plane of the human body.
Figure 16:
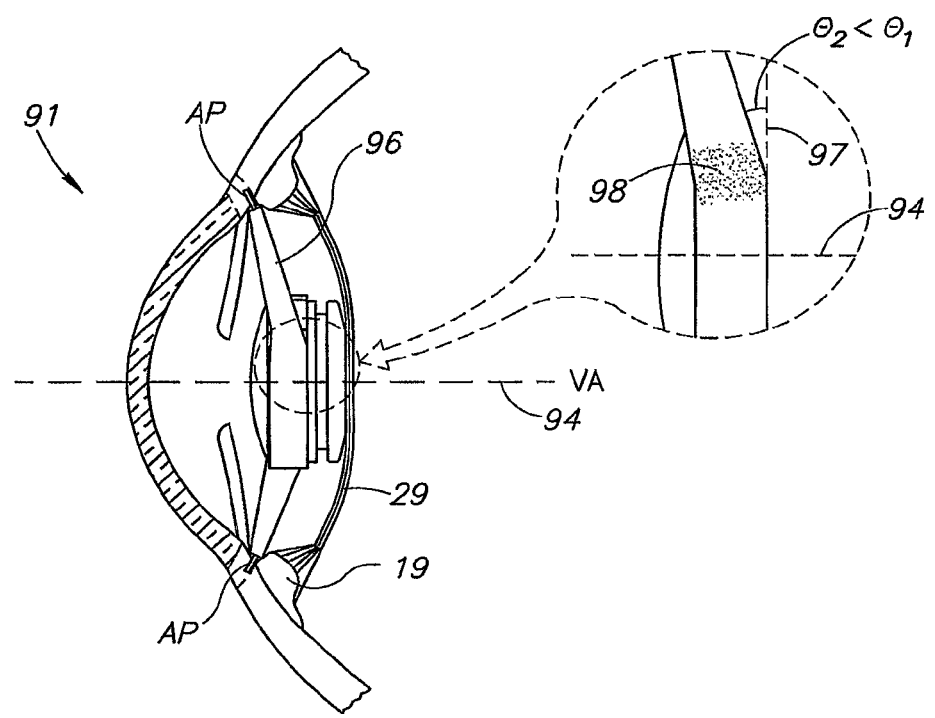
FIG. 16 is a cross section view of an anterior part of a human eye showing a subsequent position of FIG. 12's AIOL assembly along the human eye's visual axis for compensating for capsular contraction in an axial plane of the human body.

The implantation of an AIOL assembly of a variable Diopter strength in a human eye 10 after removal of its natural crystalline lens 27 is now described in connection with the AIOL assembly 31 with reference to FIGS. 10 and 11. The AIOL assembly 31 is set up such that the AIOL's longitudinal axis 48 coincides with the haptics system's longitudinal axis 36 and the annular flange 58 abuts against the main body 34 as shown in FIG. 6. The AIOL assembly 31 is typically implanted into a human eye 10 after administration of a suitable muscle relaxant for relaxing both its ciliary muscles and its iris muscles thereby dilating its pupil. The capsular diaphragm 29 has some slack by virtue of the removal of the natural crystalline lens 27. FIG. 10 shows that the haptics system's puncturing members 39 are forcibly inserted into the sclera 12 at stationary anchor points AP for retaining the AIOL assembly 31 in the annular ciliary sulcus 28. FIG. 10 also shows that the AIOL assembly 31 is deployed such that its longitudinal axes 36 and 48 are co-directional and preferably co-axial with the visual axis VA and the trailing flange 56 is urged in a posterior direction against the capsular diaphragm 29 tensioning same to become sufficiently taut to urge the AIOL 33 to its extreme compressed position as shown in FIG. 7 with maximum Diopter strength suitable for near vision purposes. Constriction of the ciliary body 19 enables the AIOL 33 to assume its extreme extended position as shown in FIG. 6 with minimum Diopter strength suitable for distance vision purposes. In the case of capsular contraction, the AIOL 33 is unable to assume its extreme extended position but rather it remains at least partially compressed depending on the degree of the capsular contraction thereby diminishing its accommodation ability. The accommodation ability of the AIOL 33 is restored by prizing open the split ring 41 and moving the AIOL 33 in an anterior direction as evidenced by the gap between the AIOL's flange 58 and the split ring 41 as seen in FIG. 11.

FIGS. 12-16 show an AIOL assembly 91 which is similar to the AIOL assembly 31 but differs therefrom in two respects: First, the AIOL assembly 91 is unitary insofar that it includes a haptics system 92 for self-anchoring implantation in a human eye's ciliary sulcus 28 at at least two stationary anchor points AP integrally formed with an AIOL 93 of variable Diopter strength. And second, the haptics system 92 has a longitudinal axis 94 and includes a pair of haptics 96 which are capable of being plastically deformed from an initial acute angle $\theta_1$ (see FIG. 15) subtended with respect to a plane 97 perpendicular to the longitudinal axis 94 to a less acute angle $\theta_2 < \theta_1$ (see FIG. 16) such that the haptics system 92 is capable of in situ selective displacement of the AIOL 93 from an initial position to a desired position along a human eye's visual axis VA. This is achieved by the haptics 96 having regions 98 adjacent the AIOL 93 impregnated with radiation sensitive bio-compatible chemicals, for example, Infra Red (IR) sensitive indocyanine green (ICG), and the like, such that the haptics 96 are plastically deformable on heating to a so-called glass transmission temperature higher than a human eye's normal 36° C. temperature but sufficiently low so as to not damage a human eye's delicate internal structures.

Figure 17:
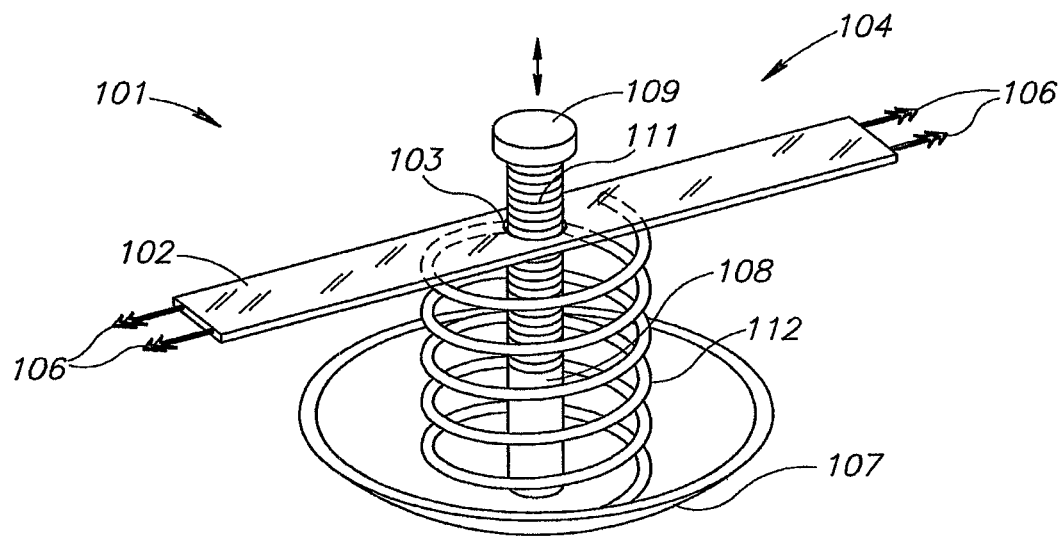
FIG. 17 is a perspective view of an accommodation measurement implant for measuring accommodation and accommodation forces in an experimental set-up including an animal eye.
Figure 18:
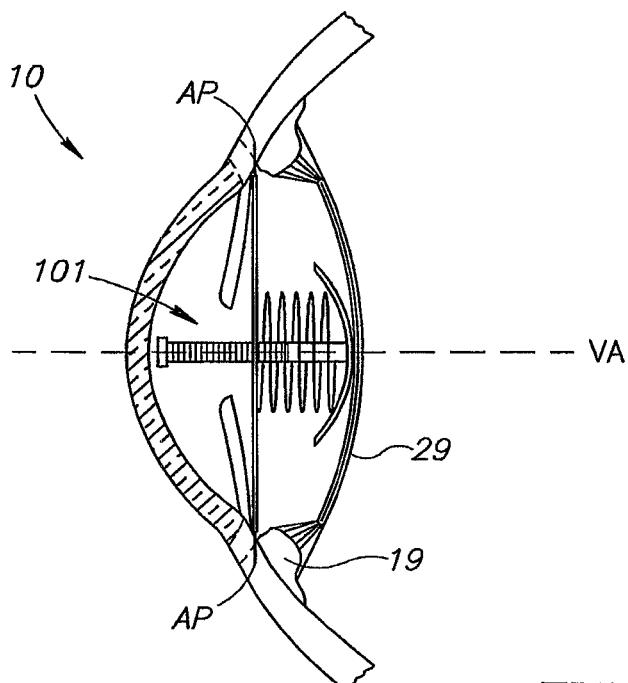
FIG. 18 is a cross section view showing deployment of the accommodation measurement implant of FIG. 17.

FIGS. 17 and 18 show an accommodation measurement implant (AMI) 101 for determining accommodation and accommodation forces in an experimental set-up including an animal eye similar to a human eye and therefore likewise numbered. The AMI 101 includes a generally rectangular rigid planar base member 102, and a central aperture 103. The base member 102 includes a haptics system 104 in the form of oppositely directed pointed puncturing members 106 for self-anchoring at anchor points AP. A convex shaped member 107 suitably shaped and dimensioned for placing on an animal eye's capsular diaphragm 29 from the anterior direction is provided with an upright pin 108 having a pinhead 109 and passing through the aperture 103. The pin 108 includes a series of graduations 111 therealong at a pitch of less than 500 μm, and preferably at 250 μm. A helical compression spring 112 is placed between the base member 102 and the convex shaped member 207 for urging them apart to be stopped by the pinhead 109 abutting against the base member 102. The base member 102, the convex shaped member 107, and the pin 108 are preferably formed of a suitable biocompatible material, for example, stainless steel, PMMA, and the like. Accommodation is determined as a function of a pin's displacement relative to the base member 102 as a result of relaxation of the ciliary body 19. Pin displacements may be detected by external devices or alternatively the graduations 111 may be inspected by a direct eye inspection. The actual forces developed by the relaxation of a ciliary body can be determined as a function of the compression spring's spring constant k and pin displacement.

While the invention has been described with respect to a limited number of embodiments, it will be appreciated that many variations, modifications, and other applications of the invention can be made within the scope of the appended claims.

What is claimed is:
1. A haptics system for retaining an accommodating intraocular lens (AIOL) in a human eye having a visual axis and including a sclera of tough connective tissue, an annular ciliary sulcus, and a sphincter-like ciliary body having a relaxed state for tensioning a capsular diaphragm in an anterior direction along the visual axis, the AIOL having an anterior surface and a posterior surface, and at least one shape memory optical element resiliently elastically deformable between a natural shape with a first Diopter strength and a deformed shape with a second Diopter strength different than the first Diopter strength whereby the AIOL has a continuously variable Diopter strength between a minimum Diopter strength for distance vision purposes and a maximum Diopter strength for near vision purposes, the haptics system comprising a main body with a longitudinal axis intended to be co-directional with the human eye's visual axis and at least two haptics tangentially extending from said main body in opposite directions in a plane perpendicular to said haptics system's longitudinal axis, and each with at least one pointed puncturing member for penetrating the tough connective tissue of the human eye's sclera for self-anchoring implantation in the human eye's annular ciliary sulcus at at least two spaced apart stationary anchor points for retaining the AIOL along the human eye's visual axis, wherein each haptic of said at least two haptics has a thin profile in said plane perpendicular to said haptics system's longitudinal axis such that said at least two haptics are sufficiently flexible for encircling around said main body and a wide profile along said haptics system's longitudinal axis for holding the AIOL rigid against a compressive force therealong such that relaxation of the human eye's ciliary body urges the human eye's capsular diaphragm against the AIOL's posterior surface from a posterior direction for affecting the AIOL's Diopter strength.

2. The system according to claim 1 wherein said wide profile tapers from a haptics' proximal end adjacent said main body towards its distal end remote therefrom.

3. The system according to claim 1 wherein said haptics system includes a tubular main body stationary relative to said at least two stationary spaced apart anchor points and is capable of being selectively manipulated in situ between a clamping state for retaining a discrete AIOL having a tubular casing with a longitudinal axis at a desired position along the human eye's visual axis and an unclamping state for enabling in situ selective displacement of the discrete AIOL to a desired position along the human eye's visual relative to said at least two spaced apart stationary anchor points.

4. The system according to claim 3 wherein said main body has an axial length L1 along its longitudinal axis and the AIOL's casing has an axial length L2 along its longitudinal axis wherein L2>L1 such that said main body is capable of fully contacting the AIOL's casing in said clamping state along an adjustment stroke longer than said main body's axial length.

5. The system according to claim 1 wherein said haptics system is integrally formed with the AIOL and said at least two haptics each have a radiation sensitive region capable of deformation on in situ irradiation with selective electromagnetic radiation for enabling in situ selective displacement of the integrally formed AIOL to a desired position along the human eye's visual axis relative to said at least two spaced apart stationary anchor points.

6. The system according to claim 5 wherein said radiation sensitive region is adjacent said main body.

* * * * *